(12) United States Patent
Chételat

(10) Patent No.: US 9,839,370 B2
(45) Date of Patent: Dec. 12, 2017

(54) METHOD AND DEVICE FOR BIO IMPEDANCE MEASUREMENT

(71) Applicant: CSEM SA, Neuchâtel (CH)

(72) Inventor: Olivier Chételat, Cudrefin (CH)

(73) Assignee: CSEM CENTRE SUISSE D'ELECTRONIQUE ET DE MICROTECHNIQUE SA—RECHERCHE ET DÉVELOPPEMENT, Grenoble (FR)

( * ) Notice: Subject to any disclaimer, the term of this patent is extended or adjusted under 35 U.S.C. 154(b) by 410 days.

(21) Appl. No.: 14/072,130

(22) Filed: Nov. 5, 2013

(65) Prior Publication Data

US 2014/0128765 A1    May 8, 2014

Related U.S. Application Data

(60) Provisional application No. 61/722,482, filed on Nov. 5, 2012.

(51) Int. Cl.
*A61B 5/053* (2006.01)
*A61B 5/00* (2006.01)

(52) U.S. Cl.
CPC .......... *A61B 5/0531* (2013.01); *A61B 5/7207* (2013.01)

(58) Field of Classification Search
CPC ..... A61B 5/053; A61B 5/0531; A61B 5/0535; A61B 5/0536; A61B 5/0537; A61B 5/0538
USPC ........................................................ 600/547
See application file for complete search history.

(56) References Cited

U.S. PATENT DOCUMENTS

| | | | | | |
|---|---|---|---|---|---|
| 3,452,743 | A | * | 7/1969 | Rieke | A61B 5/0535 600/547 |
| 3,608,543 | A | * | 9/1971 | Longini | A61B 5/0809 600/536 |
| 4,182,314 | A | * | 1/1980 | Boughton | A61B 5/0531 600/547 |
| 5,588,429 | A | * | 12/1996 | Isaacson | A61B 5/0536 600/547 |

(Continued)

FOREIGN PATENT DOCUMENTS

EP    2567657 A1    3/2013

OTHER PUBLICATIONS

EPO written opinion and search report in corresponding EP application, dated Jan. 9, 2014.*

(Continued)

*Primary Examiner* — David J McCrosky
(74) *Attorney, Agent, or Firm* — Pearne & Gordon LLP

(57) ABSTRACT

Method for bio impedance measurement on a skin surface of a living body, using a bio impedance measurement device having a sensing electrode and a pilot electrode, includes the steps of placing the sensing electrode and pilot electrode on the surface of the body; providing a guard electrode adapted to separate the surface in at least two zones, among which a sensing zone including the sensing electrode and a current injection zone including the pilot electrode; providing a controller, electrically connected to the electrodes, adapted to control the current source; and controlling the potential of the guard electrode, at least at given stopping frequencies, in order to stop current from flowing from one zone to the other.

16 Claims, 20 Drawing Sheets

(56) References Cited

U.S. PATENT DOCUMENTS

| | | | | |
|---|---|---|---|---|
| 6,961,601 | B2* | 11/2005 | Matthews | A61B 5/0408 600/372 |
| 2002/0183645 | A1* | 12/2002 | Nachaliel | A61B 5/0536 600/547 |
| 2005/0043608 | A1* | 2/2005 | Haj-Yousef | A61B 5/053 600/407 |
| 2005/0065418 | A1* | 3/2005 | Ginor | A61B 5/0536 600/345 |
| 2011/0001497 | A1* | 1/2011 | Chetelat | A61B 5/04004 324/692 |
| 2012/0143076 | A1* | 6/2012 | Wieskotten | A61B 5/053 600/547 |
| 2014/0039341 | A1* | 2/2014 | Bohorquez | A61B 5/0537 600/547 |

OTHER PUBLICATIONS

Graham, M. "Guard ring use in physiological measurements." IEEE transactions on bio-medical engineering 12.3 (1964): 197-198.*

* cited by examiner

METHOD AND DEVICE FOR BIO IMPEDANCE MEASUREMENT

TECHNICAL FIELD

The present invention relates to impedance measurement systems. More specifically, the invention allows motion-artefact-free bio impedance measurements insensitive to skin impedance.

STATE OF THE ART

In impedance measurements, an electrode is a piece of conductive material placed in contact or close to the surface of a body so that electrical interactions are possible in order to pick up the electrical potential of the body surface under the electrode and/or allow a current to flow between the electrode and the body.

Bio impedance measurements allow getting information on, for instance, respiration, EIT (electro-impedance tomography), body composition and hydration, impedance cardiography, etc. Usually, it consists in injecting, normally at some kilohertz, a small current via a pair of electrodes and measures the electrical-potential responses, either with the same but preferably other electrodes.

In the real world, bio impedance measurement systems have to cope with many challenges, such as for instance:
 high surface impedance (e.g., skin impedance),
 unstable electrode/body interface (motion artefacts),
 high impedance of electrode/body interface,
 high impedance variation of electrode/body interface (dry, sweat, motion, etc.),
 limited impedance of frontend amplifier,
 electronic noise, etc.

These last years, much progress has been made in particular regarding the frontend electronics, which offer amplifiers with more ideal characteristics than before (higher input impedance, lower input bias current, lower noise), and regarding the measurement technique that allows the use, for instance, of active dry and capacitive electrodes. The method described in EP2567657 by the same applicant allows simultaneous measurements of several bio impedances, each of them at a given frequency, but all frequencies close one to each other.

SUMMARY

A main object of the invention is to provide a method and device enabling an improvement in precision of bio impedance measurements.

Another object of the invention is to provide a method and device enabling to perform impedance measurement, regardless of motion artefacts, impedance variations of electrode/body interface, electronic noise, etc.

According to the invention, these aims are achieved notably by means of the object of the main claim, whilst the dependent claims illustrate advantageous variant embodiments of the invention.

More particularly, the invention provides a method for bio impedance measurement on a skin surface of a living body, using a bio impedance measurement device comprising a sensing electrode and a pilot electrode, comprising the following steps:
 placing said sensing electrode and pilot electrode on the surface of said body;
 providing a guard electrode (4) adapted to separate the surface in at least two zones, among which a sensing zone including the sensing electrode and a current injection zone including the pilot electrode;
 providing a controller, electrically connected to said electrodes, adapted to control the current source;
 controlling the potential of said guard electrode, at least at given stopping frequencies, in order to stop current from flowing from one zone to the other.

The method provides an efficient approach in order to increase the surface impedance and therefore avoid a current flow. Most preferably, the controller provides a high rejection within a narrow band.

In a preferred embodiment, the control of potential of said guard electrode is provided at least at frequencies enabling to substantially equal the potential of said sensing electrode.

The rejection is preferably provided within two narrow lateral bands on both sides of a given angular frequency ω. Thus, at the angular frequency ω, it is assumed that there is no disturbance current (e.g., 50/60 Hz) nor injected current (e.g., 50 kHz).

In another aspect, the invention also provides a device for bio impedance measurement at the skin surface of a living body, comprising a sensing electrode and a pilot electrode adapted for placement on a surface of a body, and further comprising a guard electrode adapted to separate the surface in at least two zones, among which a sensing zone including the sensing electrode and a current injection zone including the pilot electrode, a controller, electrically connected to said electrodes, adapted to control a current source and a controller adapted to control the potential of said guard electrode, at least at given stopping frequencies, in order to stop current from flowing from one zone to the other.

BRIEF DESCRIPTION OF THE FIGURES

Examples of embodiments of the invention are illustrated by the attached figures in particular FIGS. 1 to 10 wherein:

FIG. 11 represents electrical model of electrode/body interface;

FIG. 12 illustrates equivalent model of a real capacitive electrode;

FIG. 13 illustrates electrical circuit diagram and section of the disclosed electrical-potential pickup;

FIG. 14 shows barrier when the impedance of (3) is too low; and optimised geometry with intermediate contacts with body surface if body surface protrudes inside sensor and risks to touch the electrode (2);

FIG. 15 is another embodiment of electrical-potential pickup;

FIG. 16 illustrates management of input bias/offset current in embodiment of FIG. 15;

FIG. 17 shows a possible implementation of feedback filter F for management of input bias/offset current in embodiment of FIG. 15;

FIG. 18 illustrates management of input bias/offset current (bootstrapping) and increase of input impedance (neutralization) in embodiment of FIG. 13;

FIG. 19 illustrates capacitance and current measurement;

FIG. 20 illustrates also another method of capacitance measurement;

FIG. 21 shows embodiment of electrical-potential pickup for motion-artefact-free measurement of bio potential according to FIG. 20; and FIG. 22 illustrates also embodiment of two electrical-potential pickups for motion-artefact-free measurement of ECG and bio impedance.

DETAILED DESCRIPTION OF POSSIBLE EMBODIMENTS

Figure 1:
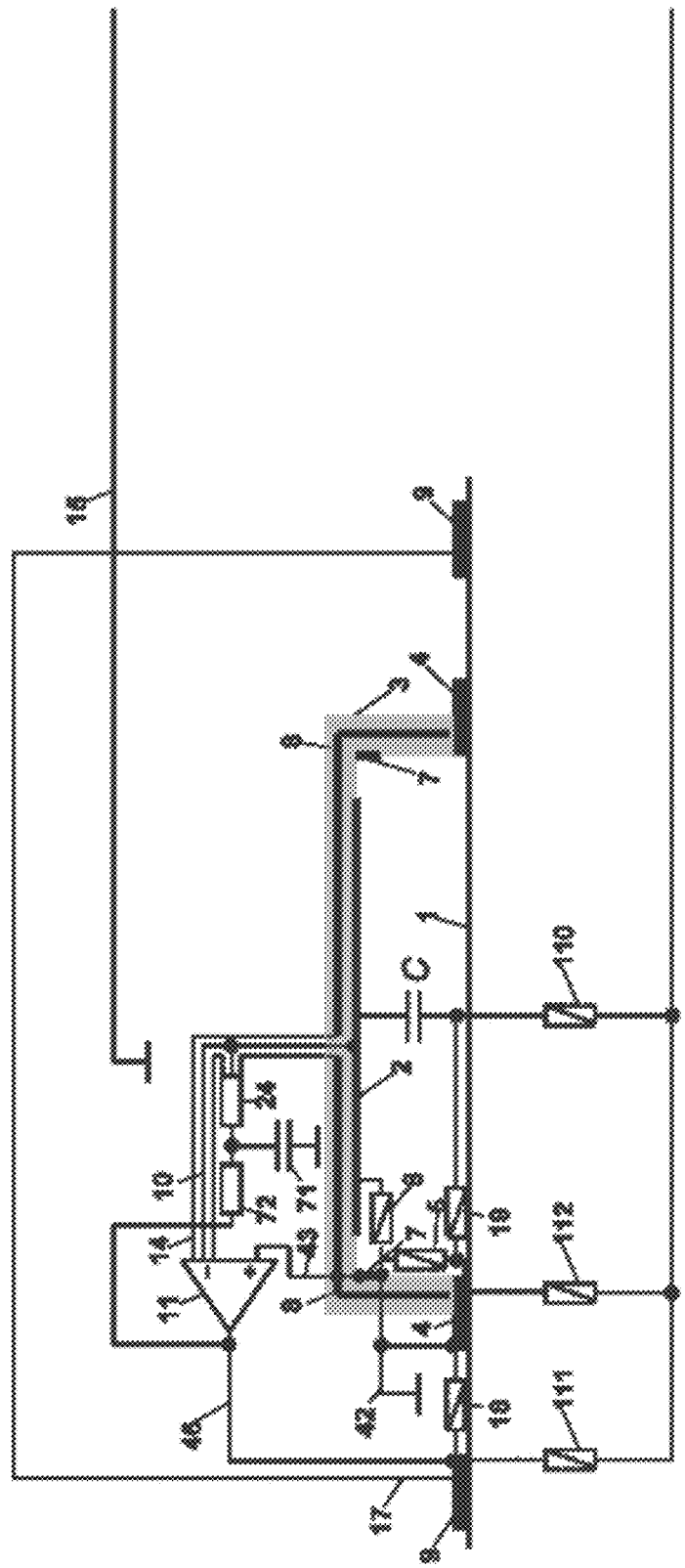
FIG. 1 shows an application of the invention to virtually increase the impedance and reduce surface current that would otherwise flows from electrode and finally through impedance.

FIG. 1 shows the invention applied to virtually increase the surface impedance (19), between the body surface (1) under the electrode (2) and the body contact (4). To this aim, the electrode (4) is now connected to ground (42) and an additional ring electrode (9) is placed around electrode (4) and driven by the operational amplifier (11) through line (46).

The virtual increase of the impedance (19) is desirable to force all current to cross the skin through impedance (111). Otherwise, a fraction of the current also flows via impedance (110), which induces a disturbance/bias on the voltage measurement. This is particularly the case if the skin is covered by a film of water, but even in dry conditions, it is an advantage to prevent the current to flow through impedance (19) and from there through impedance (110).

The currents flowing through the skin are typically for bio impedance measurements.

The embodiment of FIG. 1 is however difficult to implement in practice and is unfortunately not very effective. It is not very effective, because the ratio of impedance (18) over the impedance of the interface of electrode (4) with the skin (1) is not very high. Therefore, the real potential applied on the skin (1) may not be close enough to the potential of (2) to substantially virtually increase impedance (19).

Figure 9:
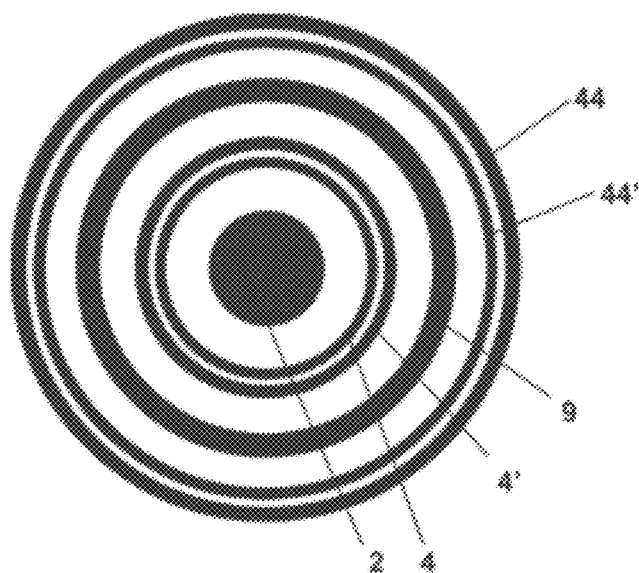
FIG. 9 illustrates a possible form factor for the five-ring implementation.

It is difficult to implement because the internal output impedance of the operational amplifier (11) makes with impedance (18) a voltage divider and low-pass filter. Other voltage dividers and low-pass filters are made by the impedance (111)/(112) and (110)/(19). These voltage dividers and low-pass filters affect the feedback open-loop transfer function of the operational amplifier (11). As the model of voltage dividers shown in FIG. 9 is simplistic and anyway with values covering large variations depending on the real conditions (i.e., dry or wet), stability or/and bandwidth are not under design control.

Figure 2:
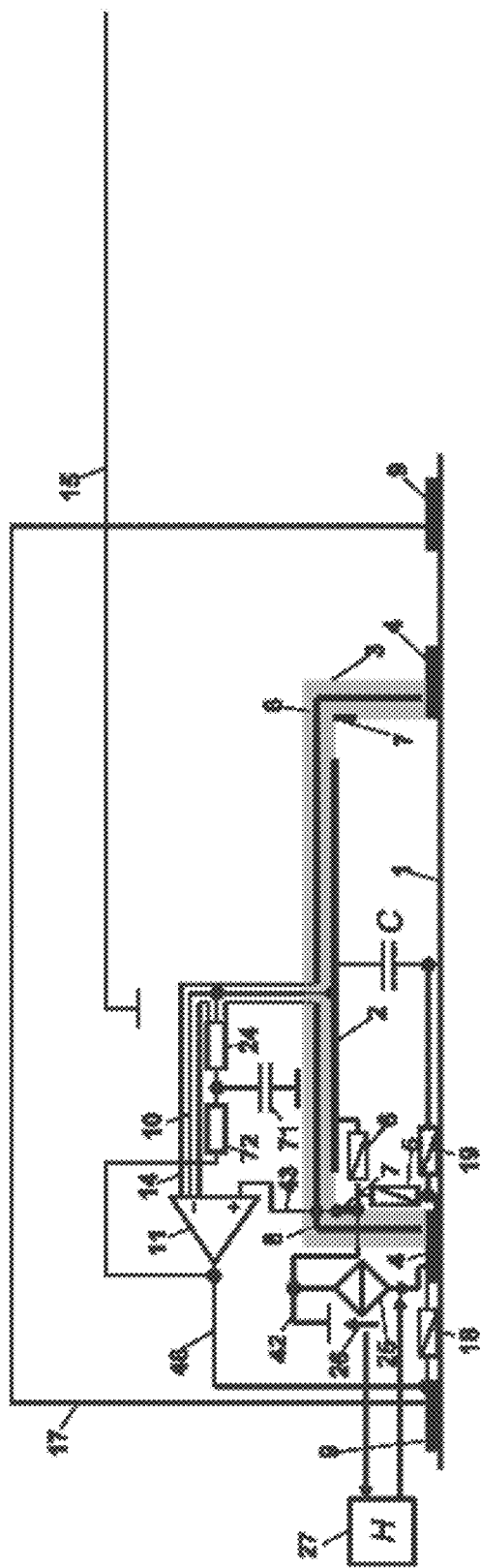
FIG. 2 illustrates an embodiment virtually increasing the impedance around specific frequencies, such as mains disturbances (50/60 Hz) for bio potential measurement or injected current (typically 50 kHz) for bio impedance measurement.

The solution to this issue is presented in FIG. 2 where a current source (25) is controlled by the controller (27) so that the voltage (26) between the electrode (4) and the ground (42) is close to zero only for a set of narrow bands to stop (e.g., 50/60 Hz, 50 kHz). Therefore, electrode (4) "disturbs" the open-loop transfer function of the operational amplifier (11) only at narrow bands, and more importantly at frequencies where the gain of the open loop is still high. Thus, stability is not affected and performances kept as high as possible in all situations (e.g., dry or wet). For frequencies outside the stopped bands, the current source (25) outputs a zero current, which means that the impedance between electrode (4) and ground (42) is high (infinite for an ideal current source).

Figure 3:
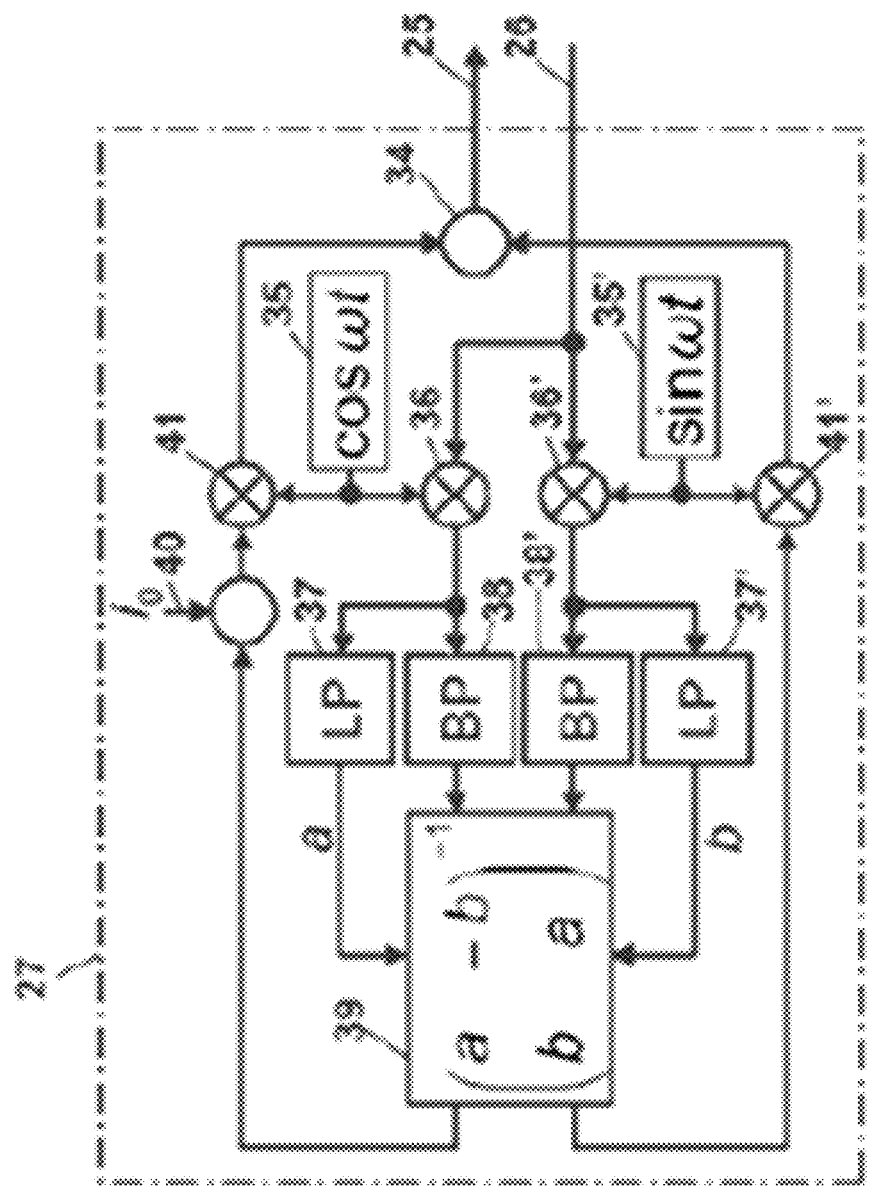
FIG. 3 illustrates a controller allowing a high rejection within a narrow band.

FIG. 3 shows the controller (27) allowing a high rejection within a narrow band. More precisely, the rejection will be performed within two narrow lateral bands on both sides of a given angular frequency $\omega$.

At the angular frequency $\omega$, it is assumed that there is no disturbance current (e.g., 50/60 Hz) nor injected current (e.g., 50 kHz). Instead, a small pilot current $i_0$ (40) is injected as a cosine wave at angular frequency $\omega$ by the current source (25). This current will allow the controller (27) to measure the phasor that converts the injected current (25) into the resulting voltage (26). The real and imaginary parts a and b of this phasor are determined by the multipliers (36) and (36'), respectively, since the voltage (26) is multiplied by the cosine wave (35) and sine wave (35'). After low-pass filtering by the low-pass filters (37) and (37') to remove the high-frequency intermodulation product, one obtains the two quasi-static signals a and b, which are the real and imaginary parts of the phasor.

The real and imaginary parts of the signal (26) on both sides of, but not on, the frequency $\omega$ are obtained with the band-pass filters (38) and (38'). Note that the gains G of these filters are also the controller gains.

Assuming that the phasor does not substantially change for frequencies in the vicinity of $\omega$, the inverse matrix (39) can be used to decouple the 2×2 MIMO system dealing with real and imaginary parts. The multipliers (41), (41') and the sum (34) reconstitute the control signal (25). Note that the dynamic is controlled by the band-pass filters (38) and (38') that do not depend on the impedance modelling the relation between the voltage (26) and the current (25). This dependency is entirely handled by the decoupling matrix (39). As decoupled MIMO systems are still stable if the decoupling is not completely perfect, the assumption made above about the phasor in the controlled band being the same as the one measured at the central frequency $\omega$ is justified.

Figure 4:
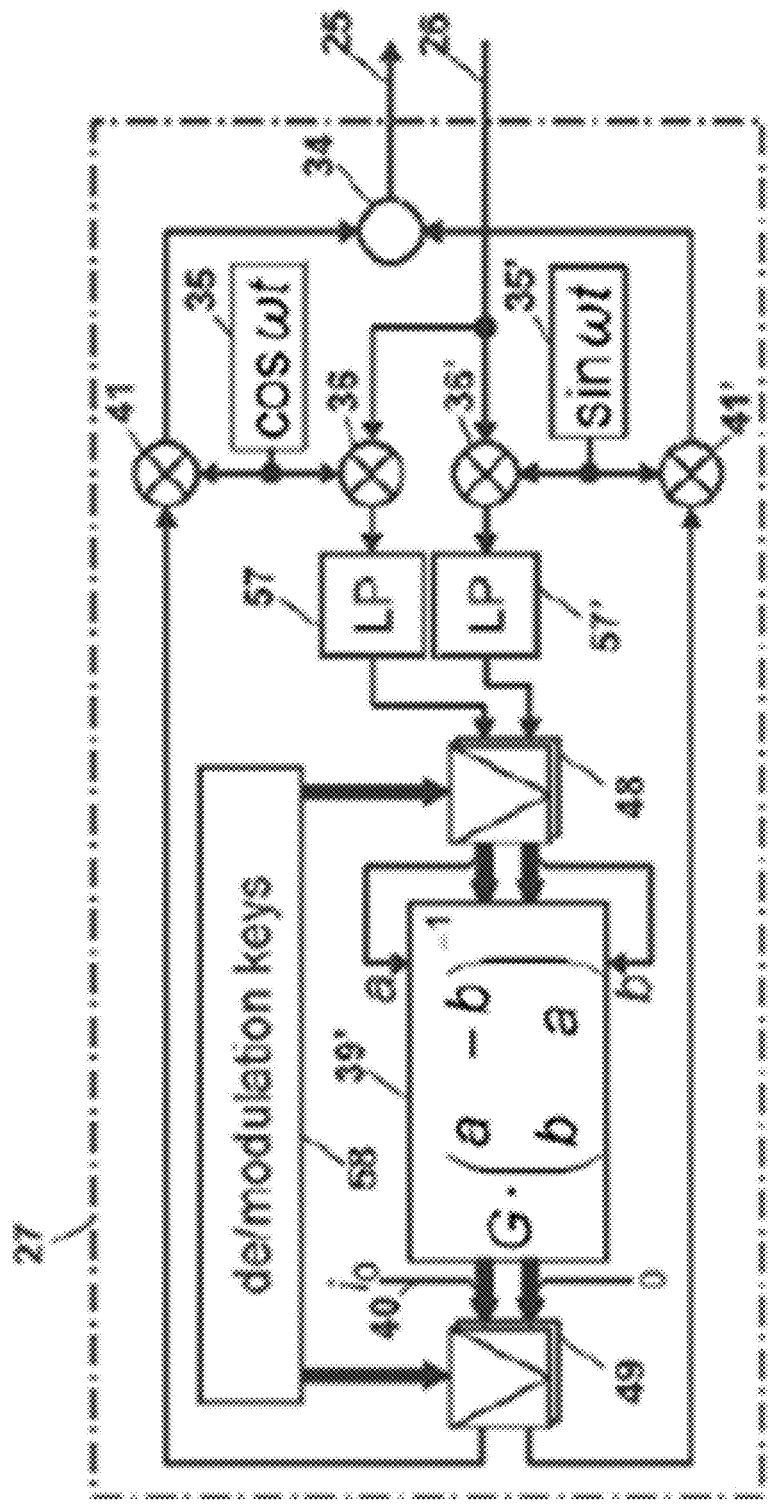
FIG. 4 shows generalisation of a controller allowing a high rejection of several modulated signals within a narrow band.

A generalisation of the method of FIG. 3 is shown in FIG. 4 where several current channels are contained within a narrow band around the frequency $\omega$. Each channel is separated with the others by modulation, which can be an amplitude modulation of cosine/sine subcarriers or any other possible modulation (e.g., time modulation, where each channel has its own time slot). The principle is that the pilot current $i_0$ (40) takes one channel and is modulated by the modulator (49) according to the modulation key provided by (58). The modulation key can be for instance a cosine/sine wave of a given frequency for an amplitude modulation, a comb of a given delay for time modulation, etc. The result is then multiplied at (41) by cos $\omega t$ (35) and at (41') by sin $\omega t$ (35') before being summed by (34) in order to control the current source (25). The resulting voltage (26) is then demodulated by a multiplication (36, 36') with the cosine/sine signals (35, 35') and low-pass filtered by (57, 57') to suppress the high-frequency intermodulation products and to retain the baseband only. The two components a and b are extracted from the cosine/sine basebands by the demodulator (48) with the same modulation key provided by (58).

At the same time, all other channels are extracted from the cosine/sine basebands according to their respective key and multiplied by the controller (39') comprising the decoupling matrix (39) and a transfer function G(s) or G(z) that can be for instance an integrator, where s is the Laplace variable used for continuous-time controllers and $z=e^{sT}$ with T as sample time for discrete-time controllers. Of course, non-LTI controllers can also be used. Each channel is then modulated by the modulator (49) according to its respective key provided by (58) and the cosine/sine basebands multiplied at (41, 41') by the cosine/sine waves (35, 35') before being summed by (34) to control the current source (25).

The advantage to control each channel independently is that one can have a much higher open-loop gain for each channel than the one of the band-pass filters (38) and (38'), and therefore the controlled current source (25) will result in a very low impedance for each channel while offering a very high impedance otherwise, in particular for the frequencies determining the stability of the operational amplifier (11).

Figure 5:
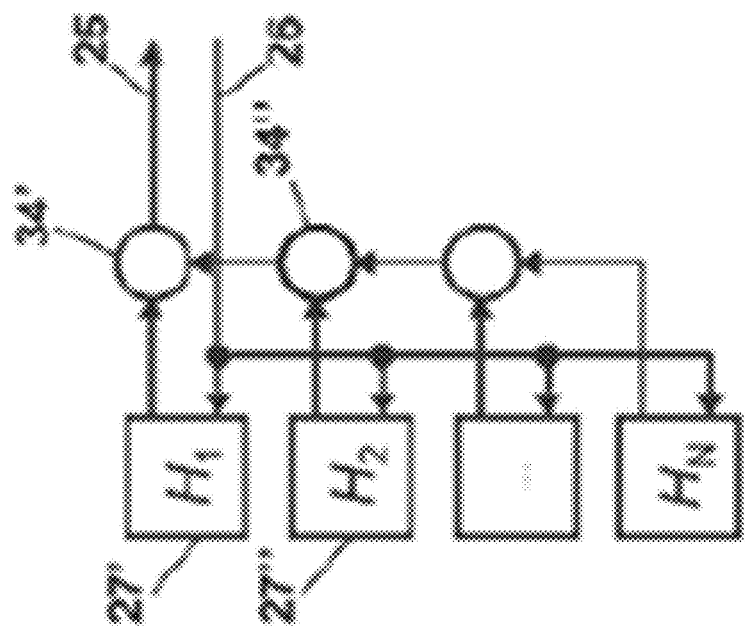
FIG. 5 illustrates a controller for the rejection of several narrow bands.

If there are several narrow bands to reject simultaneously (e.g., 50/60 Hz and 50 kHz), several controllers (27), i.e., (27'), (27"), etc. can be summed by (34'), (24") as shown in FIG. 5.

Figure 6:
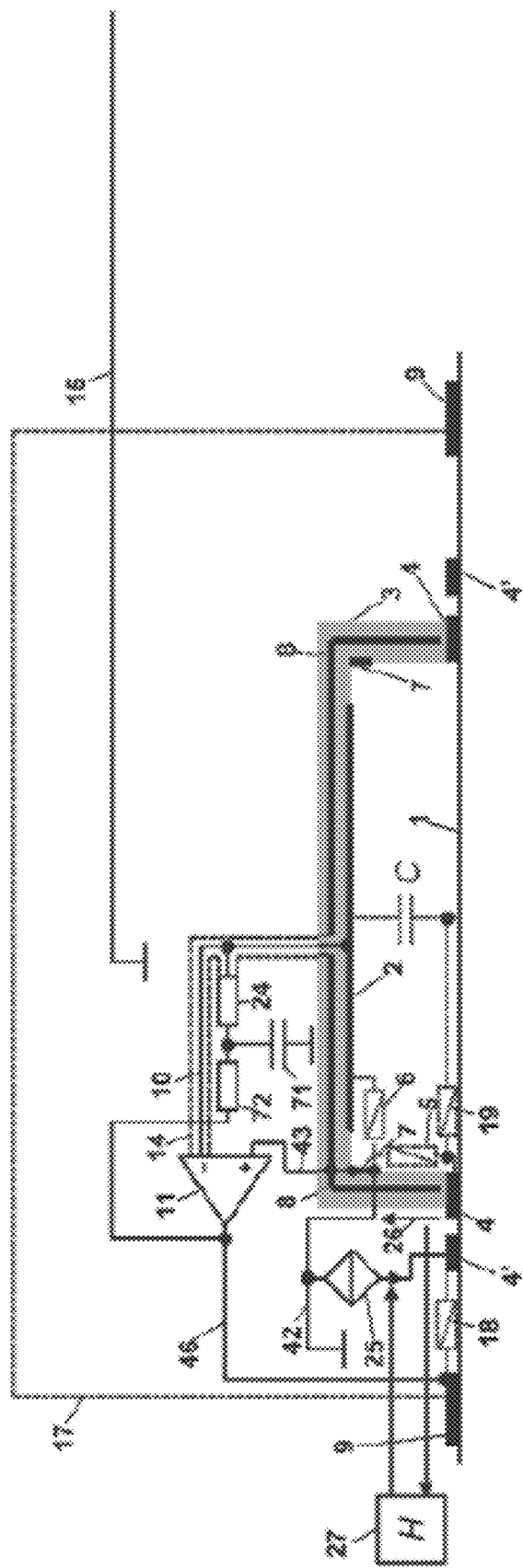
FIG. 6 illustrates a more effective implementation of FIG. 2 (split of electrode 4 into two electrodes 4 and 4' separating potential and current, respectively)

FIG. 6 shows a more effective implementation of the embodiment of FIG. 2, because separate electrodes (4) and (4') are used for sensing the voltage (26) and inject the current (25), respectively. Therefore, the impedance at the interface between the electrodes (4), (4') and the skin surface (1) does not affect the result. Alternatively, the voltage between the electrodes (4) and (2) can be taken instead of the voltage (26).

Figure 7:
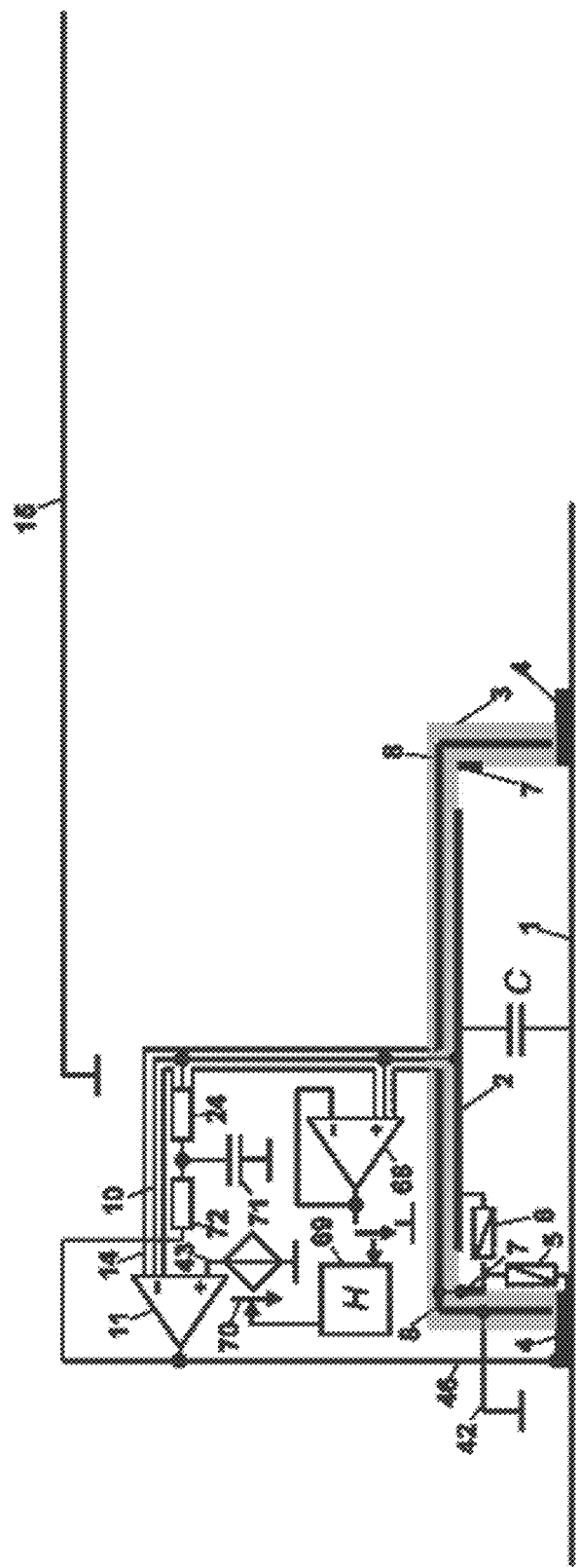
FIG. 7 illustrates another embodiment allowing additional rejection at narrow bands.

The rejection of narrow bands described in FIG. 3 to FIG. 5 can also be applied to the embodiments addressing the conductor (7) in order to enhance the rejection of the operational amplifier (11) on additional narrow bands of interest. To this aim, the voltage between the electrode (2) and the ground (42) is controlled closer to zero for narrow bands by increasing the open-loop gain for these bands. A possible embodiment is shown in FIG. 7 where the potential of the electrode (2) is sensed by the follower (68). The resulting voltage is then filtered by the feedback filter H (69) implemented according to FIG. 3, FIG. 4 and/or FIG. 5, and the result controls the controlled voltage source (70).

Additionally or alternatively, the transfer function H (69) can as well increase the feedback gain for the loop (10-46) at low frequency. For example, a I(PI) controller can be built, the integrator I being the one of the operational amplifier (11) and the I of the PI the additional transfer function H, P being equal to unity. A higher gain at low frequency is of course desirable to improve the performance of the virtual increase of the impedance (6). This is especially important when the impedance (6) is low.

To further illustrate the invention, the following examples are provided, with no intention to limit the scope of the invention.

Figure 8:
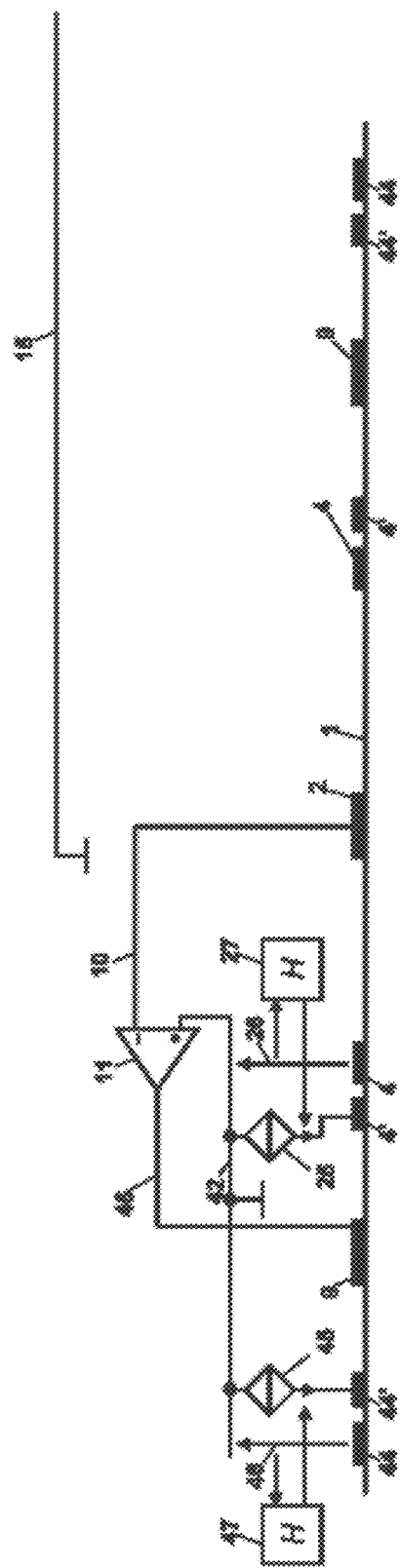
FIG. 8 illustrates a five-ring implementation.

FIG. 8 shows the principle of a five-ring implementation with the central electrode that can be a capacitive electrode as shown in all previous figures, or a resistive electrode. The idea of electrodes (44) and (44') is the same as for electrodes (4) and (4'), i.e., to isolate the controlled potential of electrode (9) in order not to be disturbed or affect the other electrical-potential pickups or the connection (15) that may not be insulated, and not to disturb the central sensing electrode, respectively. With the invention, all current is injected in the region under electrode (9).

Figure 10:
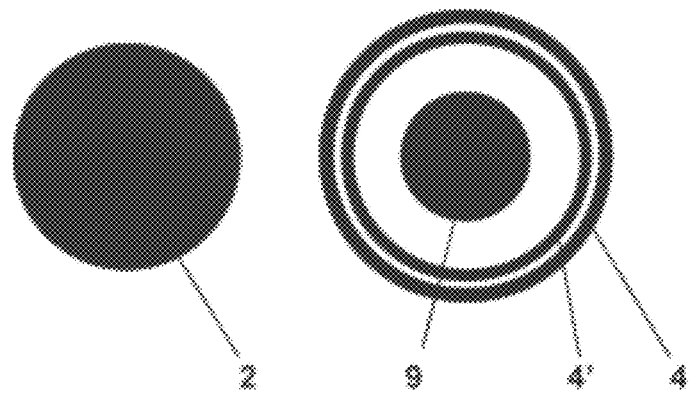
FIG. 10 illustrates a two-disc embodiment.

FIG. 9 shows a possible form factor for the five-ring implementation of FIG. 8. Alternatively, a two-disc embodiment as shown in FIG. 10 is also possible. In FIG. 10, only the disc (9) has rings (4') and (4), but in another embodiment, the disc (2) has also its ring (4') and (4).

The present invention also relates to electrical-potential pickups distributed over a human/animal body or body part. The invention allows motion-artefact compensation techniques to be effective in normal conditions, i.e., without requiring extremely clean and dry pickup housing.

Bio potential measurements are used for instance for ECG (electrocardiogram), EEG (electroencephalogram), EMG (electromyogram), etc., where the difference between two bio potentials or between one bio potential and a reference potential is of interest.

Even though in practice gel $Ag/Ag^+Cl^-$ electrodes are still widely used and (sometimes tough) skin preparations recommended, today it is possible to get good signals with more gentle and user-friendly electrodes.

Figure 11:
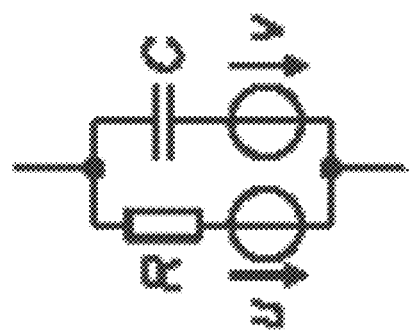

If we assume that the input impedance of the frontend amplifier is high enough to cope with impedance variations of electrode/body interface and that its noise is negligible (which are assumptions easily reachable nowadays), most of the trouble comes from the electrode/body interface. This interface can be modelled in a first approximation as shown in FIG. 11. Note that the same model applies for capacitive or resistive (i.e., gel or dry) electrodes, but the relative importance of the different parts is significantly different.

For resistive electrodes, the voltage u has its greatest component from the electrochemical cell (gel or wet electrode) or from the different electronic affinity of the two materials in contact (dry electrode). This voltage can easily be of the order of half a volt and varies slowly with temperature, ion concentration, etc. Another contribution comes from the thermal noise of the resistance R.

The voltage v has a DC component $v_0$ modelling the initial voltage (at time t=0) of the capacitance C, which is created by u for resistive electrodes and by the ambient electric field (of the order of 100 V/m) for capacitive electrodes. For capacitive electrodes, the input bias current of the frontend amplifier may also contribute to the initial DC component of voltage v.

The AC component of voltage v(t) is mainly due to motion artefacts that changes the capacitance C(t) in the absence of charge exchanges as shown in the first equation below. The second equation is derived from the first one assuming a plate capacitor with a distance d between the plates. AC means relatively high frequency components, while DC means relatively low frequency components.

$$v(t) = \frac{C_0}{C(t)} v_0$$

$$v_{AC} = \frac{d_{AC}}{d_{DC}} v_{DC}$$

As $v_0$ or $v_{DC}$ may not be negligible, the variation of capacitance due to motion artefacts is usually the main source of noise both for resistive and capacitive electrodes.

The above second equation is useful since it allows one to simplify a step further the model of FIG. 11 assuming that C remains constant (this is not true, but acceptable since the most relevant effect of the capacity variation is taken into account in v thanks to the second equation). A model with assumed constant C and R is necessary to derive an LTI (linear time invariant) transfer function. With this assumption, the resulting voltage between the two terminals is:

$$u_e = \frac{u + RCs \cdot v}{1 + RCs}$$

where s is the Laplace variable. This equation shows that the RC circuit filters u with a low-pass filter and v with a high-pass filter (first order with cut-off frequency $f_c = 1/2\pi RC$).

Therefore, for resistive electrodes, RC should be small to minimize the motion artefacts arising from v.

Moreover, small impedance is also desirable to minimize the effect of voltage divider between the varying electrode impedance and the input impedance of the frontend amplifier. Therefore, the input impedance and the area of the electrode should be maximized. Note that the RC product is independent of the electrode area since R is inversely proportional and C proportional to the electrode area.

However, low RC does not help filter the voltage u. Therefore, the noise of u has to be limited by other ways, such as giving preference to stable interfaces, like Ag/Ag$^+$ Cl$^-$ electrode material with gel. The interface skin/gel is however more difficult to control. The skin stratum corneum is sometimes removed by abrasion in order to reduce the effect of this interface on the noise u.

The model of FIG. 11 is too simplistic to be used for effective motion-artefact compensation in the case of resistive electrodes (gel or dry). For instance, the resistance R and the capacitance C depend on the frequency. For capacitive electrodes that do not touch the body or the clothes, i.e., for capacitive electrodes that have air (or any other gas) as dielectric, the model is however excellent. For these electrodes, the capacitance C is small but close to ideal (linear and constant at all frequencies). This feature opens the way towards motion-artefact compensation techniques based on the model of FIG. 11. Moreover, as there is no direct contact, no other interface exists. Therefore, the only source of electrode noise seems to be the voltage v (i.e., motion artefacts). This is however not the case in real conditions as shown below.

Assuming that the low frequencies are not of interest and filtered with a first-order high-pass filter with cut-off frequency $f_L$ (e.g., at $f_L$=0.05 Hz for ECG), the thermal noise generated by the resistor R is filtered with a low-pass filter by the capacitance C and eventually results in the following voltage on the electrode:

$$u_{e,th} = \sqrt{\frac{k_B T}{C(1 + 2\pi f_L RC)}}$$

where $k_B$ is the Boltzmann constant, and T the temperature. For example, the RC constant in air would be:

$RC = \in \rho \approx 8.85 \text{ pF/m} \cdot 40 \text{ T}\Omega\text{m} = 350 \text{ s}$ where $\in$ is the air permittivity and $\rho$ the air resistivity.

Furthermore, a capacitance disc of φ1 cm at a uniform distance of 1 mm from the body surface with air in between would lead to:

$C=0.7$ pF, $R=510$ TΩ, $u_{e,th}=7.3$ μV$_{rms}\approx 44$ μV$_{pp}$

This noise is not negligible, since for ECG, the standard 60601-2-47 requires a maximum of 50 μV$_{pp}$ (which means that the noise budget is almost already reached only with thermal noise). Resistivity of air can vary a lot and depends on its composition. The value chosen above (40 TΩ m) is assumed to be fair.

The most important point is that a resistance of R=510 TΩ is huge and it is very likely that the impurities (e.g., a fingerprint, a drop of sweat that dried out, or simply a water condensation film) on the housing walls from the capacitance plate up to the body surface contact (needed to keep the 1 mm distance with the body surface) will not reach such high value in practice.

Figure 12:
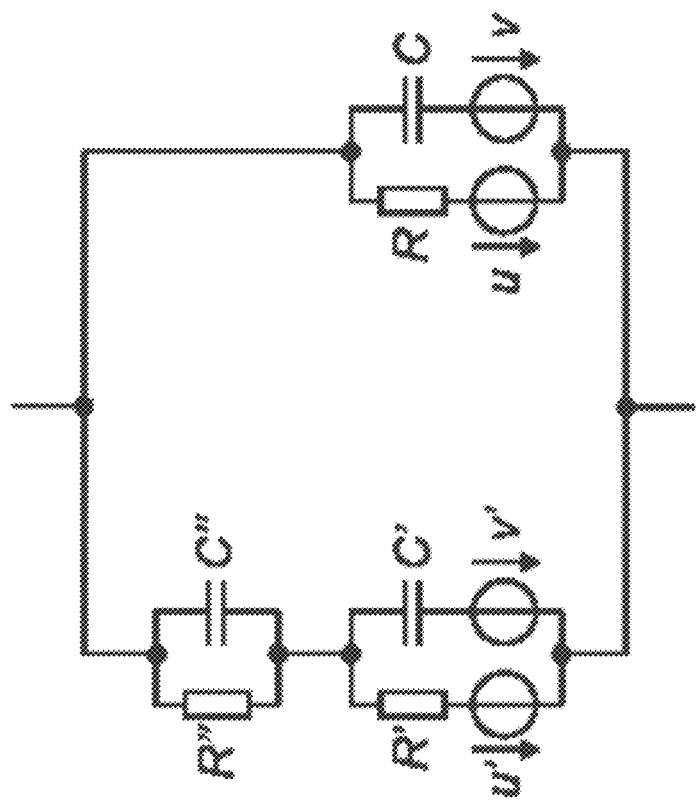
FIGS. 11 to 22 illustrate another aspect of the invention related to bio potential measurements.

FIG. 12 shows the equivalent model of a real capacitive electrode. The RC circuit on the right is the one discussed so far. On the left, the R"C" circuit models the surface impedance of the housing walls. Finally, the R'C' circuit is the model of the dry electrode made by the housing in contact with the body surface.

The capacitance C" can be considered as negligible with respect to C (if it was not the case, the situation would just be even worse). In a real situation, it is assumed that the extremely high resistance R is negligible with respect to R". The impedance of the circuit R'C' is negligible with respect to the impedance R"C". Therefore, the circuit of FIG. 12 can be reduced to the circuit of FIG. 11 with C and v unchanged, but R being dominated by R", and u being the resulting noise of the dry electrode made by the housing in contact with the body surface, i.e., v' filtered by R'C'.

The first negative impact of taking into account realistic wall-surface impedance is that the value of the resistance R to be taken into account in the above equation is significantly lower, with unacceptable results on thermal noise.

Moreover, since the housing contact with the body surface makes a standard dry electrode, even if the housing is not conductive, motion makes this interface a noise source for u that can be filtered out only when RC is sufficiently great.

Assuming that the motion artefacts originating from the capacitive electrode itself (voltage v) can be handled by any of the methods described in U.S. Pat. No. 8,193,821 or in US Patent no US 2012/0116198, the electrical-potential pickup could be made insensitive to motion artefacts. If however, the surface resistance from the housing contact with the body surface to the capacitive electrode plate is smaller than about 5 TΩ, nothing will have been gained regarding motion artefacts (since the RC low-pass filter of FIG. 11 will no longer filter out all noise from u). Even worse, the much more complex capacitive electrode sensor (which would also add its own electronic noise in addition to not fully compensate the motion artefacts) will have a thermal noise about 10 times above the 60601-2-47 requirement, i.e., much worse than what could be obtained just with a dry electrode. Finally, the area used for the capacitive electrode could have been used for a larger (i.e., less noisy) dry electrode. Therefore, the absolute minimum for the surface resistance in the above example must be at least 500 TΩ.

Frontend amplifiers with high input impedance can be made as described in U.S. Pat. No. 6,961,601 or U.S. Pat. No. 7,885,700. These patents explain how to deal with the input bias current of the frontend amplifier while obtaining very high input impedance (bootstrapping, guard, and neutralization). Another approach is disclosed in US Patent no US 2011/0001497 where a floating frontend amplifier (FFA) providing a more robust and higher increase of input impedance than neutralization is described. Both approaches can also be combined.

Another object of the invention is to provide a sensor structure that electrically substantially increases the apparent surface resistance or impedance around any potential-sensing electrode in order to guarantee that the effect of the surface resistance or impedance in normal usage condition (i.e., for surface not extremely clean and dry) is negligible.

In other words, with the invention, most of R in the model of FIG. 11 will be due to the air dielectric leakage resistance of the capacitive electrode.

Figure 13:
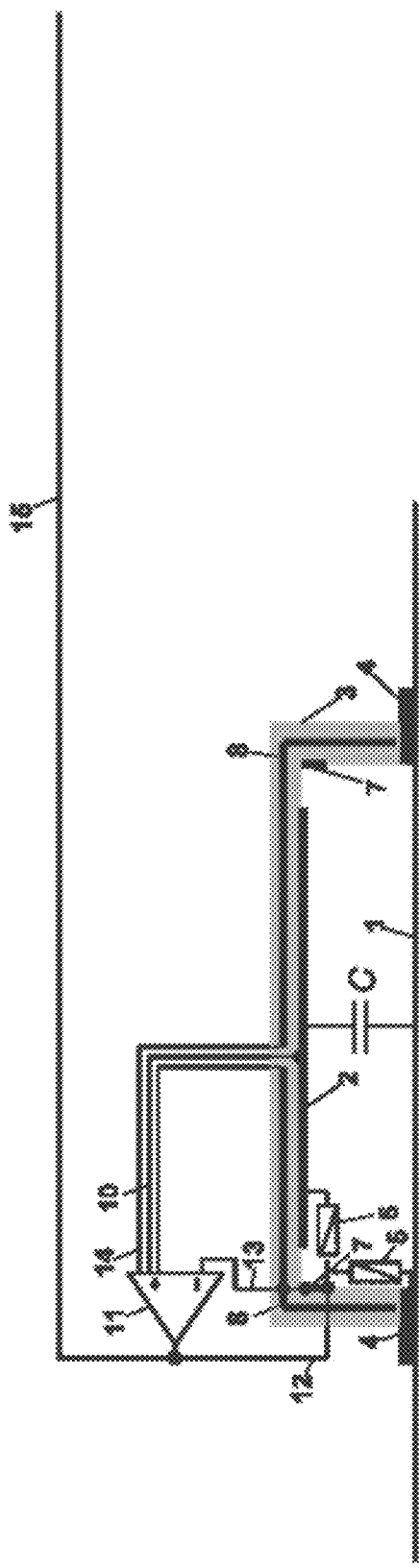

FIG. 13 shows one of the simplest embodiments of the invention. An electrical-potential pickup is placed on a body surface (1), such as for instance the skin. The electrical-potential pickup is in contact with the surface at (4), for instance as a ring. Even though it is not the preferred configuration, it is also possible to have a layer of clothes between the body surface (1) and the electrical-potential pickup.

The electrical-potential pickup function is to transform the high input impedance (1/Cs) of the electrical-potential source into a low-impedance electrical-potential source driving the conductor (15).

The capacitance C may be the result of the body surface (1) and the conductor (2) making the two capacitor plates and of a cavity of the electrical-potential pickup filled with air or any other gas as dielectric. Note that the conductor (2) can be or not be covered with a layer or film of solid dielectric.

The cavity enclosure (3) is mostly a dielectric of low resistive leakage including a guard (8). The main object of the invention is to provide a solution to the too-low surface leakage impedance (5 in series with 6) between the capacitance plate (2) and the electrical-potential pickup in contact with the body surface at (4). To this aim, a conductor (7) is inserted between the capacitance plate (2) and the body contact (4) so as to surround the capacitance plate (2). The conductor (7) is preferably part of the surface so as to allow galvanic connection, but it can possibly be totally or partially covered with a thin layer of solid dielectric when capacitive coupling is sufficient. The conductor (7) and the capacitance plate (2) are separated by a portion of dielectric (3) and the surface impedance between them is modelled by (6). Similarly, the conductor (7) is preferably not in contact with the body surface (1) or contact (4) since a portion of dielectric (3) with surface impedance (5) is inserted in between.

The potential of the capacitance plate (2) is sensed by the positive input of the operational amplifier (11) connected via the line (10) preferably guarded with (14). The guard (14) is electrically connected or at least at the same potential as the guard (8). The negative input of the operational amplifier (11) is connected to the guard (8) and to the conductor (7) via the line (13). In a preferred embodiment, this connection to the conductor (7) is made at the side closest to the capacitance plate (2), whereas the other side closest to the body contact (4) is connected to the output of the operational amplifier (11) via the line (12). The output (15) of the electrical-potential pickup is also connected to the output of the operational amplifier (11).

Figure 18:
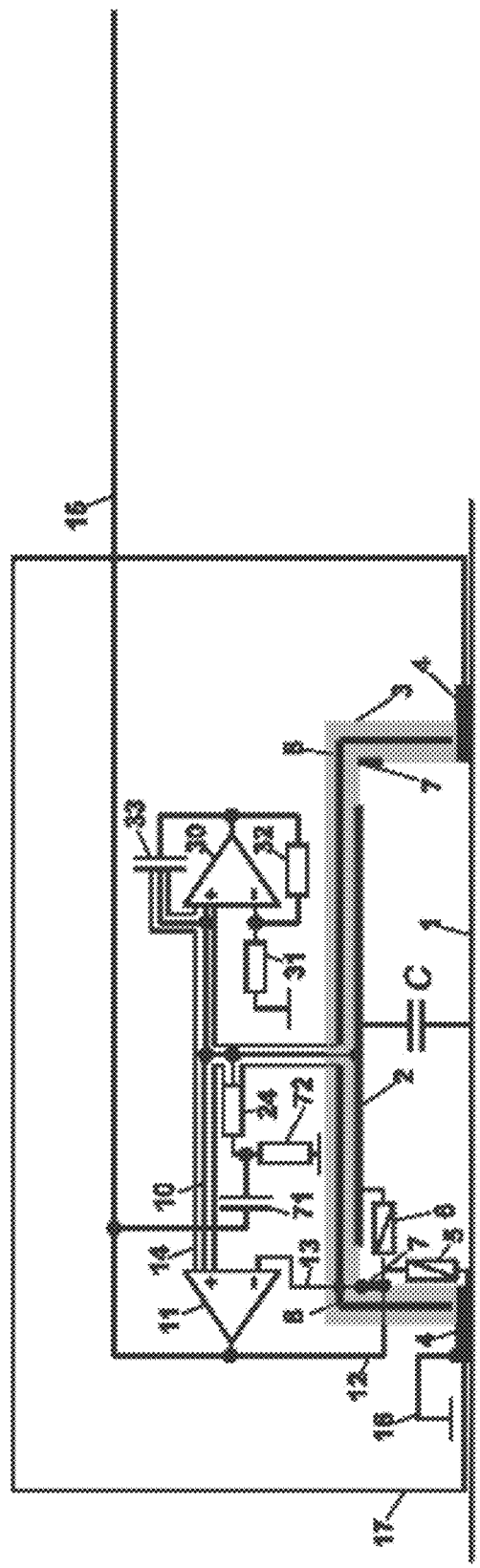

The operational amplifier (11) is mounted as a follower with the negative feedback made by the lines (12, 13) and conductor (7). Therefore, the potential of conductor (7) closely follows the potential of the capacitance plate (2). This prevents any surface current to flow between the capacitance plate (2) and the conductor (7), virtually magnifying the impedance (6) by g+1, where g is the gain of the operational amplifier (11). The conductor (7) is preferably not in contact with the contact (4) so as to keep the impedance (5) at a sufficiently high value for stability reason when the ground is connected to the body skin (1). Such connection can be for instance when the body contact (4) is grounded as shown in FIG. 18 with line (16).

The conductor (7) does not have infinite conductivity in practice. As it is of paramount importance for best performance to have the potential of the conductor part (7) close to the capacitance plate (2) the closest to the potential of the capacitance plate (7), the sense line (13) is connected at this end, while the other end of the conductor (7) is connected to the output of the amplifier (11). Therefore, any current flowing to the ground from line (12) via impedance (5) does not induce a voltage drop degrading the magnification of impedance (6).

Until now, the impedance of the dielectric (3) has been considered infinite. If this assumption does not properly model the reality, one can as well separate the dielectric (3) with the conductor (7) as shown in FIG. 14.

Figure 14:
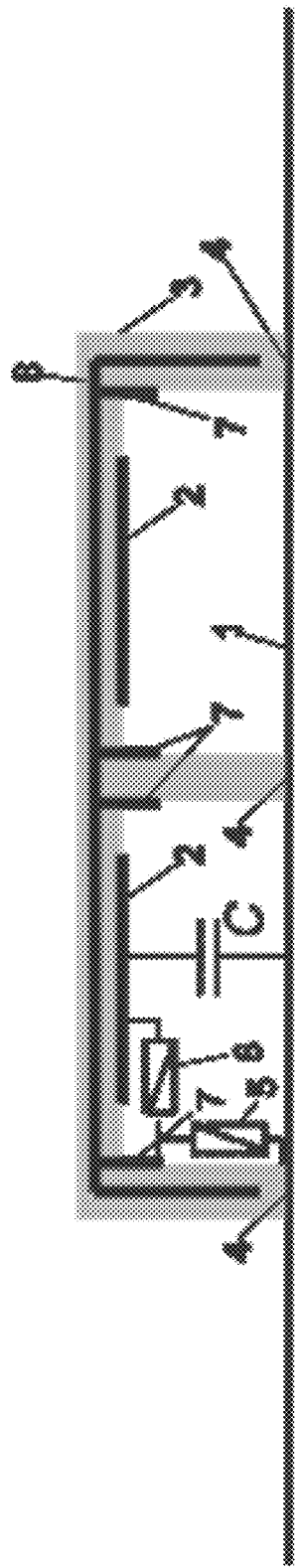

To avoid that the skin (1) protrudes inside the sensor and comes in contact with the capacitance plate (2) or conductor (7), the geometry of the pickup can be optimised and have intermediate contacts (4) with the body surface (1) as illustrated in FIG. 14.

Figure 15:
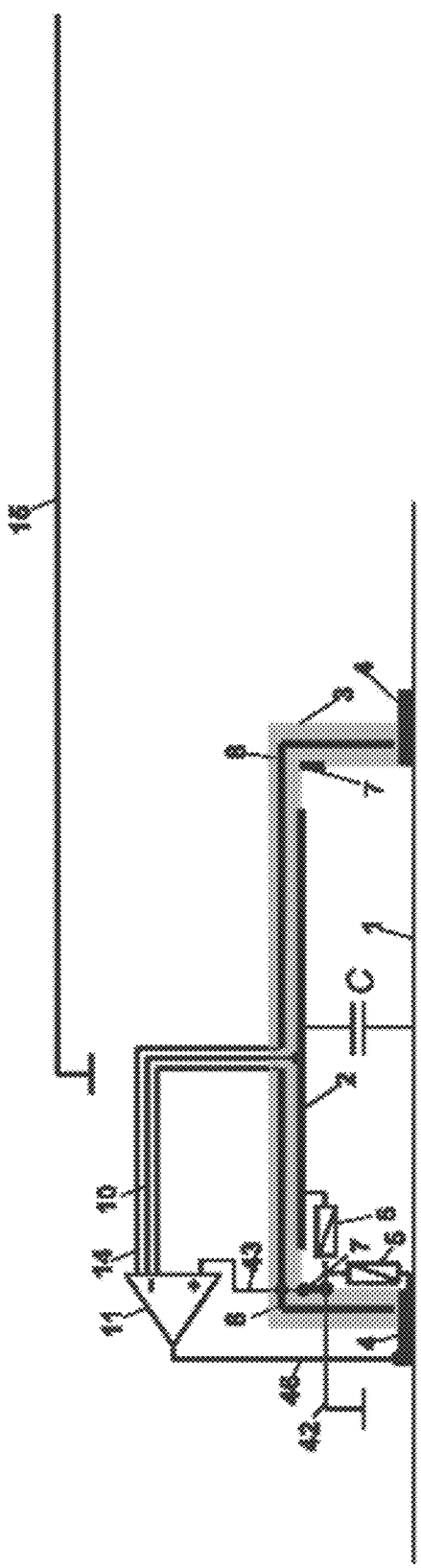

Another embodiment is shown in FIG. 15. This embodiment assumes that the operational amplifier (11) and internal ground (42) are floating for each electrical-potential pickup. Such floating frontend amplifiers are easily obtained for instance with a unique power supply (e.g., battery) for each electrical-potential pickup. A unique power supply would also provide another interesting feature: any current from line (15) will flow first to the ground, then to the power supply of the operational amplifier (11), exit at the output of the operational amplifier (11), and eventually cross the skin from electrode (4) up to the body core. However, the embodiment of FIG. 13 also shares this property when electrode (4) is connected to ground and when each electrical-potential pickup has its own battery as power supply and ground.

Nevertheless, the embodiment of FIG. 15 has a unique feature: the input impedance of the frontend amplifier, i.e., of the operational amplifier (11), is magnified by g+1, where g is the gain of the operational amplifier (11). This is because the ground (42) closely follows the amplifier input connected to line (10) thanks to the feedback applied on the electrode (4) by the operational amplifier (11).

Unlike the embodiment of FIG. 13, the negative input of the operational amplifier (11) is connected to the capacitance plate (2) via line (10), whereas the positive input is connected to the guard (8), to the conductor (7), and finally to the ground (42).

The potential of line (15) closely follows the potential of the capacitance plate (2), which itself follows the picked-up bio potential because of the extremely high virtual input impedance of the operational amplifier (11) made by the feedback (46). Therefore, the current flows freely from line (15) to the body core with a voltage drop close to zero, i.e., like if there was a pass-through of zero ohm instead of the high skin impedance. This feature is highly desirable for bio potential measurements because any disturbance current arising, for instance, from the well-known 50 Hz/60 Hz mains through stray capacitances is eliminated. It is also desirable for bio impedance measurements since the skin impedance is not only high, it also fluctuates with variations of pressure exerted by the electrical-potential pickup on the body surface.

As for FIG. 13, the same preference applies for connecting the conductor (7) to the operational amplifier (11) at the side closest to the capacitance plate (2) and to the ground (42) at the side closest to the electrode (4).

In real implementations, operational amplifiers have an input bias/offset current different from zero. Therefore, the circuit of FIG. 15 cannot work, since this input bias current will be integrated by the capacitance C until the voltage at line (46) reaches saturation. Moreover, operational amplifiers also have a voltage offset different from zero. Such a voltage will be applied on the impedance (6) which will also result in a current integrated by the capacitance C.

Figure 16:
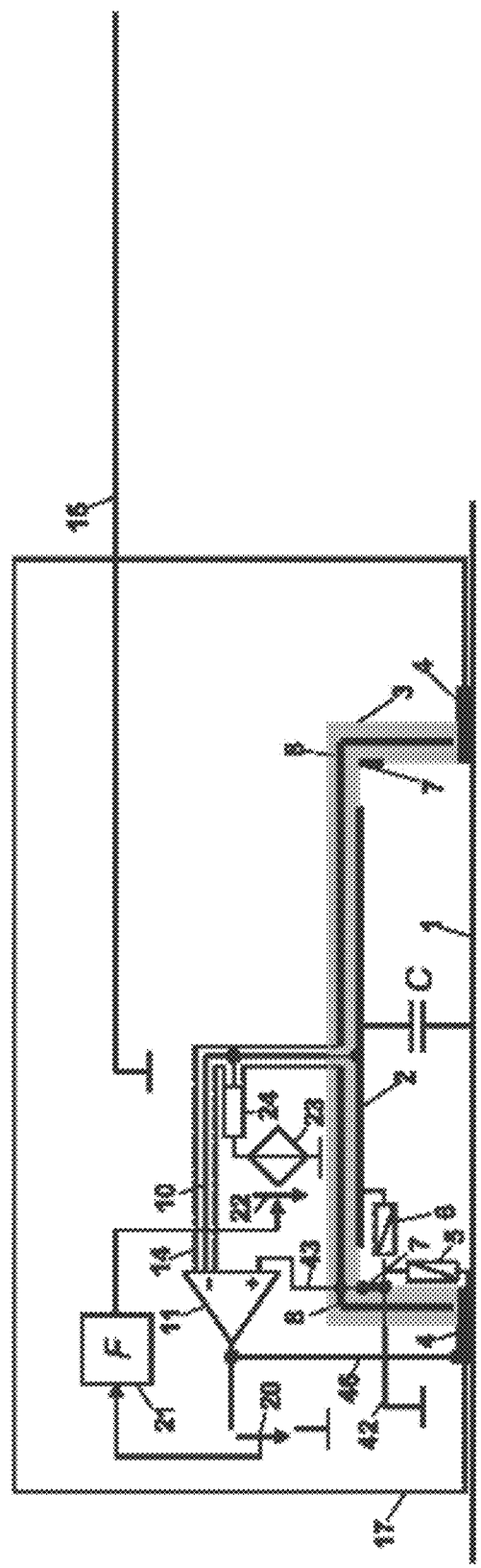

In order to compensate for these two currents, FIG. 16 shows an improved embodiment in which a current source is controlled so that the voltage (20) between line (46) and ground is close to zero or at least never reached saturation. As a matter of fact, the current source is implemented in FIG. 16 as a controlled voltage source (23) in series with the impedance (24). An ideal current source would have an internal impedance (24) infinite. In FIG. 16, the impedance (24) can be high since the currents to compensate for are small. Moreover, as the potential on line (10) is close to ground thanks to the operational amplifier (11), the current source implemented by the voltage source (23) in series with the impedance (24) is nearly ideal.

Figure 17:
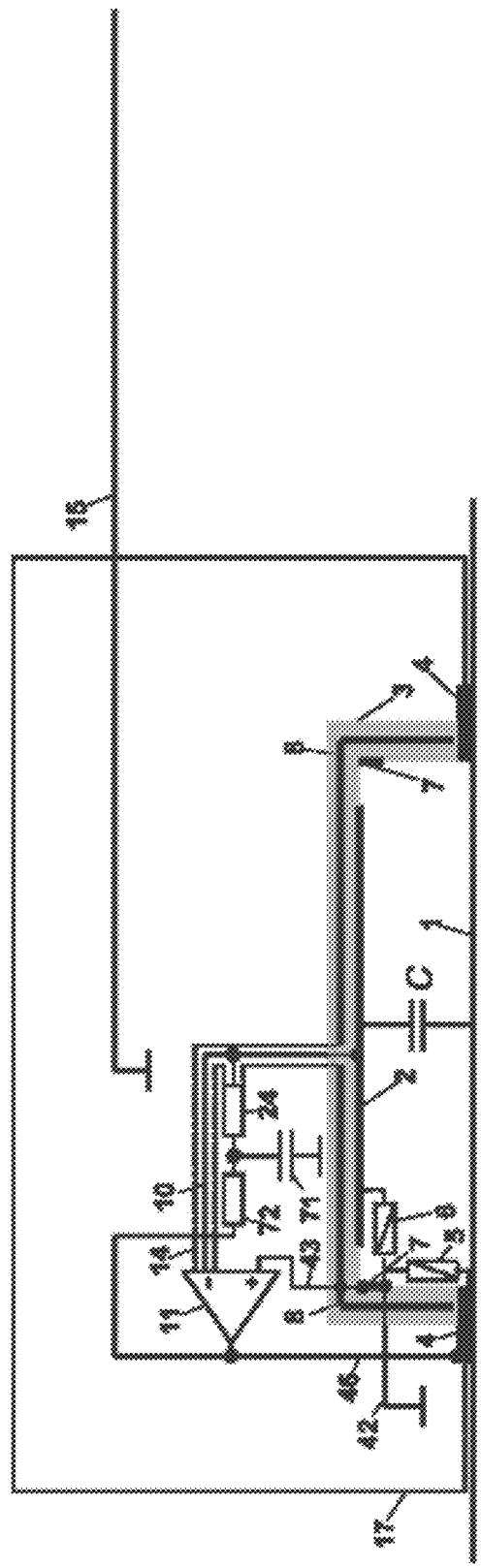

The feedback filter F is typically a gain or preferably a low-pass filter so as to have a steeper cut-off. It can be implemented analogically or digitally with a real voltage source (23), or simply with passive components as shown FIG. 17, where the output of the operational amplifier (11) is in series with a resistance (72) connected at the same time to the impedance (24) and to the ground via a capacitance (71).

The shield (17) will help make the electrical-potential pickup compliant with respect to EMC regulations (electromagnetic compatibility). The shield (17) can be connected to the electrode (4) or to the ground.

FIG. 18 shows a similar strategy for the management of the input bias/offset current in the embodiment of FIG. 13. The feedback filter F (21) may also be implemented in a similar way as in FIG. 17, but with the capacitance (71) connected to the output of the operational amplifier (11) and the resistance (72) to the ground. This technique is also well known as bootstrapping (since the follower has a positive feedback). As the potential of line (10) does not follow the ground potential, note however that the current source implemented by the voltage source (23) is less ideal than the one described above FIG. 16.

Moreover and for the same reason, the input impedance of the operational amplifier (11) may not be high enough for capacitive measurement. A too-low input impedance has well-known negative effect regarding change of skin impedance due to variation of pressure for resistive electrodes. For capacitive electrodes, the problem is different since the capacitance C in series with the skin impedance is anyway dominant. High input impedance is required so that the voltage divider made by the capacitance C and the input impedance hardly reduces the measured potential. If this condition is not fulfilled, the potential of the guards (8) and (14) will not be equal and the stray capacitance will no vanish. More importantly is that the same effect applies for the invention which requires that the conductor (7) is at the very same potential as the one of the capacitance plate (2).

Therefore, a technique called neutralization is used to increase the input impedance for the configuration of FIG. 13. The operational amplifier (30) with the two resistances (31) and (32) amplifies the input voltage. The gain must be greater than unity, because the voltage on the capacitance (33) must induce a current flowing towards line (10). With proper sizing, this current will compensate for the current sunk by the input impedance of the operational amplifiers (11) and (30), as well as by the guards (14) and (8). It is however well known that such feed forward compensation technique is very sensitive to change of parameters (with temperature or aging, for instance). Moreover, because this approach requires tuning, it is usually more expensive and the increase of input impedance is limited to about an order of magnitude. To the contrary, the embodiments based FIG. 15 use a feedback loop and do not suffer from these limitations. Therefore, the preferred embodiments of the invention are all based on the one of FIG. 15, which in addition requires fewer components.

Figure 19:
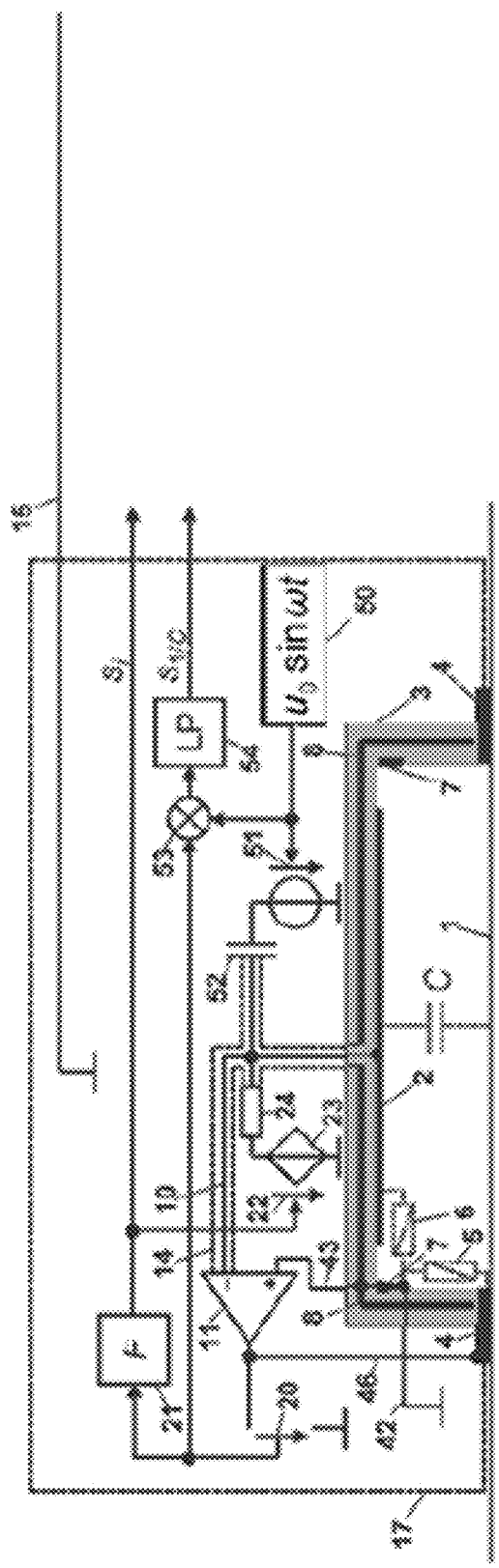

FIG. 19 shows the invention complemented with a charge source implemented as a voltage source (51) in series with a capacitance (52). The applied voltage is for instance a sine wave of constant frequency within the kilo- to megahertz range. The injected charges will induce on the capacitance C the following voltage:

$$v(t) = \frac{C_{52}}{C(t)} u_0 \sin \omega t$$

where $C_{52}$ is the capacitance (52), and $\omega$ the angular frequency of the sine wave.

This voltage is equal to the voltage (20) since the potential of the capacitance plate is controlled to ground by the operational amplifier (11). Therefore, the multiplier (53) followed by the low-pass filter LP (54) provides a signal $s_{1/C}$ proportional to 1/C. Formally, we have:

$$s_{1/C}(t) \propto LP * \left( \frac{\sin^2 \omega t}{C(t)} \right) \propto \frac{1}{C(t)}$$

where * is the convolution operator and $\propto$ the proportionality symbol.

The current injected into the capacitance C is easy to measure, since it is proportional to the voltage (22), and therefore to the signal $s_i$.

Figure 20:
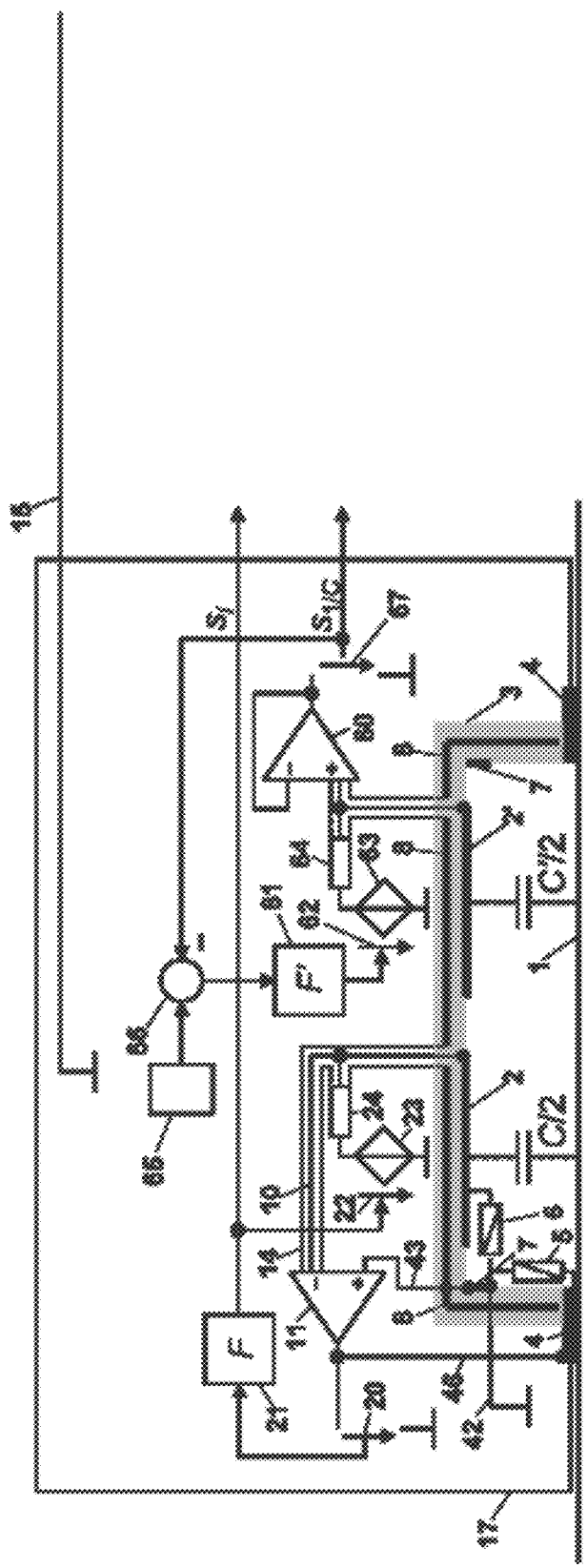

The signal $s_{1/C}$ can also be measured without the need of a multiplier as shown in FIG. 20. The principle of this other method is to split the capacitance plate (2) into two parts, so as to have the capacitances C/2 and C'/2. The capacitance C/2 is used to pick up the bio potential in exactly the same way as shown above. However, the capacitance C'/2 plate (2') has its DC potential controlled to $v_0$ by the controller F' (61) acting on the current source injecting a current in C'/2. Just as before, in this context, DC means relatively low frequencies and AC relatively high frequencies. The controller F' (61) does not control the AC component and therefore, for AC, the current is zero. Note that this current source is implemented in FIG. 20 as a voltage source in series with the impedance (64), as for the source (23). The follower (60) just buffers the potential measured on the capacitance plate (2').

Assuming that C/2=C'/2 for all times, the voltage (67), i.e., the signal $s_{1/C}$ is proportional to 1/C. Formally, we have:

$$s_{1/C}(t) = v_0 C_0 \frac{1}{C(t)}$$

where $C_0$ is the capacitance C(t) at time 0.

Figure 21:
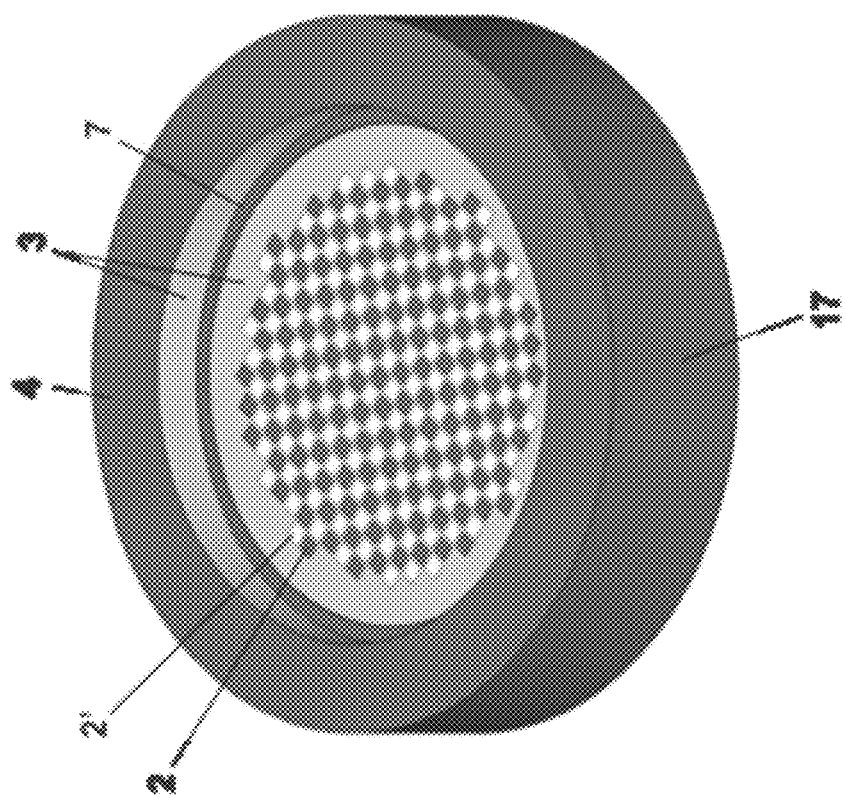

FIG. 21 shows a possible implementation of the two capacitance plates (2) and (2'). They are actually fragmented in several small pieces so that C/2 is equal to C'/2 for all times. Note that in FIG. 21, the conductor (7) of the invention is placed on the bottom of the cavity and not on the wall like drawn in the previous figures. There is no specific reason for doing this except to insist that there are several ways of placing the conductor (7).

The hollow electrical-potential pickups of the invention are also well suited to be used as suction electrode.

Figure 22:
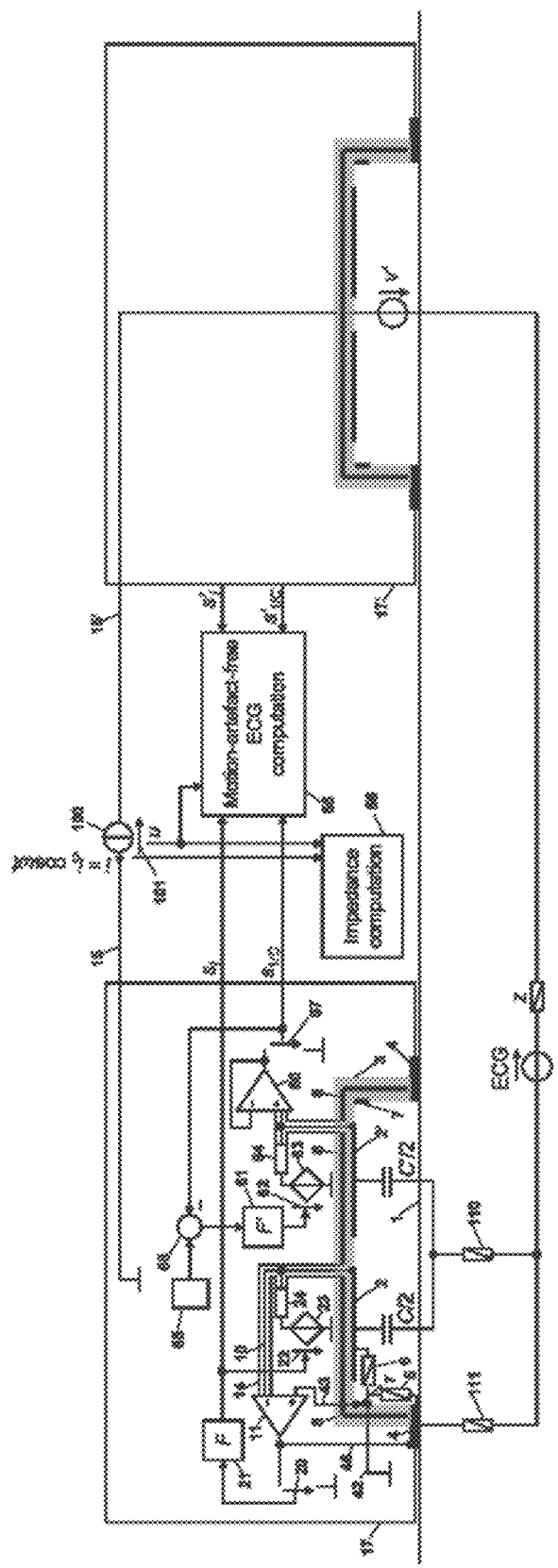

FIG. 22 shows the use of two electrical-potential pickups as described above to measure a motion-artefact-free ECG and a bio impedance, such as for respiration.

Both electrical-potential pickups can be identical, but have their own power supply (typically a rechargeable battery or an energy scavenging system). The main purposes of the electrical-potential pickup are:

- to allow a real capacitive electrode (2) measurement not affected by normal housing surface impedance (object of the invention);
- to transform the intrinsic high skin impedances (111) and (110) into a virtually zero-ohm impedance as symbolised on the right pickup;
- to measure additional information ($s_{1/C}$ and $s_i$) so as to remove the capacitance voltages v and v' that would otherwise create motion artefacts on the ECG (or other bio voltages);
- to inject a current i and measures the induced voltage so as to determine the bio impedance.

Note that line (46) can also be connected to (15') instead of (4).

In the ECG frequency band, the voltage u (101) can be seen as a sum of the real ECG voltage and of the capacitance voltages v and v' (motion artefacts) as shown in the following equation:

$$\underline{u} = \underline{ECG} + \underbrace{\begin{pmatrix} s_{1/C} \int_0^t s_i \cdot dt \\ s_{1/C} \\ s'_{1/C} \int_0^t s'_i \cdot dt \\ s'_{1/C} \\ 1 \end{pmatrix}^T}_{A} \underbrace{\begin{pmatrix} \alpha \\ \beta \\ \alpha' \\ \beta' \\ \gamma \end{pmatrix}}_{\theta}$$
$$\underbrace{\phantom{XXXXXXXXXXXXXXXX}}_{v-v'}$$

If one assumes that the ECG signal is not correlated with the motion artefacts, the ECG signal can be extracted from u by the least-square method:

$$ECG = b - A \underbrace{(A^T A)^{-1} A^T b}_{\theta}$$

Note that in the equation above $A^T A$ might sometimes be singular. However if this is the case, this only means that θ cannot be obtained explicitly. It does not mean that $A(A^T A) A^T$ is not finite and that it cannot be computed.

Of course, the weighted or iterative least-square methods or other similar adaptive filtering methods can also be used.

For the bio impedance measurement, a small cosine-wave current $i = i_0 \cos \omega t$ at a frequency outside the ECG band (typically 50 kHz) is injected by the current source (100). The following equation can be used to compute the impedance z from the resulting voltage u:

$$z(t) = LP * \frac{u(t) \cdot e^{j\omega t}}{i_0}$$

where e is Euler's number and j is the square root of −1.

The invention claimed is:

1. A method for bio impedance measurement on a skin surface of a living body, using a bio impedance measurement device comprising a sensing electrode and a pilot electrode, comprising the following steps:
    placing said sensing electrode and pilot electrode on the surface of said body;
    providing a guard electrode connected to a current source, the guard electrode being adapted to separate the surface into at least two zones, among which are a sensing zone including the sensing electrode and a current injection zone including the pilot electrode;
    providing a controller, electrically connected between the guard electrode and a ground, adapted to control the current source for controlling the potential of said guard electrode in order to set the voltage between the guard electrode and ground close to zero, at stopbands that stop current from flowing from one zone to the other.

2. A method according to claim 1, wherein the control of potential of said guard electrode is provided at frequencies enabling to substantially equal the potential of said sensing electrode.

3. A method according to claim 1, wherein the current is stopped from flowing from one zone to the other at the stopbands by providing a rejection within two lateral bands on both sides of a given angular frequency ω.

4. A method according to claim 1, wherein a pilot current i0 is injected as a cosine wave at angular frequency ω by the current source, enabling the controller to measure a phasor that converts current from the current source into a resulting voltage.

5. A method according to claim 1, in which said bio impedance measurement device is provided with a conductor and wherein a control of a potential of said conductor is performed by an operational amplifier in which an input is connected to said sensing electrode and an output is connected to said conductor.

6. A method according to claim 5, wherein an output of the operational amplifier is connected to a side of said conductor the furthest from said sensing electrode and a side of said conductor that is closest from said sensing electrode is connected to a negative input of the operational amplifier so that said conductor is part of a feedback loop of the operational amplifier.

7. A method according to claim 1, wherein said guard electrode is in electrical interaction with said body surface and said pilot electrode.

8. A method according to claim 1, wherein the living body is a human body.

9. A device for bio impedance measurement at a skin surface of a living body, comprising:
    a sensing electrode and a pilot electrode adapted for placement on the skin surface of a body,
    a guard electrode connected to a current source, the guard electrode being adapted to separate the surface into at least two zones, among which are a sensing zone including the sensing electrode and a current injection zone including the pilot electrode,
    a controller, electrically connected between the guard electrode and a ground, adapted to control the current source and further adapted to control a potential of said guard electrode so as to set the voltage between the guard electrode and ground close to zero, at stopbands that stop current from flowing from one zone to the other.

10. A device according to claim 9, wherein said guard electrode is at least partially covered by a dielectric layer.

11. A device according to claim 9, wherein said guard electrode is not in direct electrical contact with said sensing electrode or said pilot electrode.

12. A device according to claim 9, further comprising a conductor, wherein a control of the potential of said conductor is performed by a connection to said ground which is set to a potential of said sensing electrode by an operational amplifier that has its positive input connected to the ground, its negative input to said sensing electrode, and its output to either electrode in electrical interaction with said surface.

13. A device according to claim 12, wherein ground is connected to a side of said conductor that is closest from said sensing electrode.

14. A device according to claim 9, wherein an electrode is placed beside said guard electrode on the same said surface and in the same said zone as said pilot electrode and wherein a potential of the electrode is controlled by a controlled current source controlled by an output of said controller operating on a voltage between the potential of said guard electrode and a potential substantially equal to a potential of said sensing electrode.

15. A device according to claim 9, wherein the guard electrode and another separate electrode are in electrical contact.

16. A device according to claim 9, wherein the controller is made of a plurality of controllers, each controller having the same input and wherein an output is the sum of each controller output.

* * * * *

UNITED STATES PATENT AND TRADEMARK OFFICE
CERTIFICATE OF CORRECTION

PATENT NO. : 9,839,370 B2
APPLICATION NO. : 14/072130
DATED : December 12, 2017
INVENTOR(S) : Olivier Chételat It is certified that error appears in the above-identified patent and that said Letters Patent is hereby corrected as shown below:

On the Title Page

Item (73), should read:
(73) CSEM CENTRE SUISSE D'ELECTRONIQUE ET DE MICROTECHNIQUE SA - RECHERCHE ET DÉVELOPPEMENT, Neuchatel (CH)

Signed and Sealed this
Twelfth Day of November, 2019

Andrei Iancu
*Director of the United States Patent and Trademark Office*